United States Patent [19]
Hwang et al.

[11] Patent Number: 5,948,814
[45] Date of Patent: Sep. 7, 1999

[54] GENISTEIN FOR THE TREATMENT OF CYSTIC FIBROSIS

[75] Inventors: Tzyh-Chang Hwang; Arnold L. Smith; Peter Konig; Lane L. Clarke, all of Columbia; Elmer M. Price, Hartsburg; Leah A. Cohn, Columbia, all of Mo.

[73] Assignee: The Curators of the University of Missouri, Columbia, Mo.

[21] Appl. No.: 09/027,238

[22] Filed: Feb. 20, 1998

Related U.S. Application Data

[60] Provisional application No. 60/038,885, Feb. 20, 1997.

[51] Int. Cl.$^6$ ............................. A01N 43/16; A61K 31/35
[52] U.S. Cl. ......................... 514/456; 514/457; 514/460; 514/851
[58] Field of Search ..................................... 514/456, 457, 514/460, 851

[56] References Cited

FOREIGN PATENT DOCUMENTS

WO 97/43643    11/1997    WIPO ..................................... 514/310

OTHER PUBLICATIONS

Akiyama et al., Genistein, a specific inhibitor of tyrosine–specific protein kinases. *J. Biol. Chem.* 262: 5592–5595, 1987.

Baukrowitz et al., Coupling of CFTR Cl$^-$ channel gating to an ATP hydrolysis cycle. *Neuron* 12: 473–482, 1994.

Berger et al., Identification and regulation of the cystic fibrosis transmembrane conductance regulator–generated chloride channel. *J. Clin. Invest.* 88: 1422–1431, 1991.

Bradbury et al., Regulation of plasma membrane recycling by CFTR, *Science* 258: 530–582, 1992.

Carson et al., The two nucleotide–binding domains of cystic fibrosis transmembrane conductance regulator (CFTR) have distinct functions in controlling channel activity. *J. Biol Chem.* 270: 1711–1717, 1995.

Cheng et al., Defective intracellular transport and processing of CFTR is the molecular basis of most cystic fibrosis. *Cell* 63: 827–834, 1990.

Collins et al., Cystic Fibrosis: molecular biology and therapeutic implications, *Science* 256: 774–779, 1992.

Dalemans et al., Altered chloride ion channel kinetics associated with the ΔF508 cystic fibrosis mutation. *Nature* 354: 526–528, 1991.

Denning et al., Processing of mutant cystic fibrosis transmembrane conductance regulator is temperature–sensitive. *Nature* 358: 761–764, 1992.

Drumm et al., Chloride conductance expressed by ΔF508 and other mutant CFTRs in Xenopus cocytes. *Science* 254: 1797–1799, 1991.

Frizzell, et al., Altered Regulation of Airway Epithelial Cell Chloride Channels in Cystic Fibrosis. *Science* 233: 558, 1986.

Gadsby et al. The CFTR chloride channel of mammalian heart. *Annu. Rev. Physiol.* 57: 387–416, 1995.

Gunderson et al., Conformational states of CFTR associated with channel gating; the role of ATP binding and hydrolysis. *Cell* 82: 231–239, 1995.

Gunderson et al., Effects of pyrophosphate and nucleotide analogs suggest a role for ATP hydrolysis in cystic fibrosis transmembrane regulator channel gating. *J. Biol. Chem.* 269: 19349–19353, 194.

Haws et al., CFTR in Calu–3 human airway cells; channel properties and role in cAMP–activated Cl$^-$ conductance. *Am. J. Physiol.* 266 (*Lung Cell, Mol. Physiol* 10): L502–L512, 1994.

Haws et al., ΔF508–CFTR channels: kinetics, activation by forskolin, and potentition by xanthines. *Am. J. Physiol.* 270 (*Cell Physiol.* 39): C1544–C1555, 1996.

Huang et al., Genistein inhibits protein histidine kinase. *J. Biol. Chem.* 267: 15511–15515, 1992.

Hunter, Protein kinases and phosphatases: the Yin and Yang of protein phosporylation and signaling. *Cell* 80: 225–236, 1995.

Hwang et al., Regulation of the gating of cystic fibrosis transmembrane conductance regulator Cl channels by phosphorylation and ATP hydrolysis. *Proc. Natl. Acad. Sci USA* 91: 4698:4702, 1994.

Illek et al, Alternate stimulation of apical CFTR by genistein in epithelia. *Am. J. Physiol.* 270 (*Cell Physiol.* 39): C265–C275, 1996.

Illek et al., Cyclic AMP–independent activation of CFTR Cl channels by the tyrosine kinase inhibitor genistein. *Am. J. Physiol.* 258 (*Cell Physiol.* 37): C886–C893, 1995.

Lehrich et al., Tyrosine phosphorylation is a novel pathway for regulation of chloride secretion in shark rectal gland. *Am. J. Physiol.* 269 (*Renal Fluid Electrolyte Physiol.* 38): F594–F600, 1995.

Li et al., The cystic fibrosis mutation (ΔF508) does not influence the chloride channel activity of CFTR *Nat. Genet.* 8: 311–316, 1993.

Markovits et al., Inhibitory effects of the tyrosine kinase inhibitor genistein on mammalian DNA topoisomerase II. *Cancer Res.* 49: 5111–5117, 1989.

Messina et al., Soy intake and cancer risk: a review of in vitro and in vivo data. *Nutr. Cancer* 21: 113–131, 1994.

Ramsey, Management of pulmonary disease in patients with cystic fibrosis. *NEJM.* 335: 179–188, 1996.

Reenstra et al., CFTF chloride channel activation by genistein: the role of serine/threonine protein phosphatases. *Am. J. Physiol.* 271 (*Cell Physiol.* 40): C650–C657, 1996.

(List continued on next page.)

*Primary Examiner*—Frederick Krass
*Attorney, Agent, or Firm*—Kohn & Associates

[57] ABSTRACT

A method of treating cystic fibrosis by generating cystic fibrosis transmembrane conductance regulator (CFTR) function in cells containing mutant CFTR and the therapeutic composition for treatment are described. The method of treatment comprising administering an effective amount of genistein, or genistein analogues and derivatives, to a person afflicted with cystic fibrosis.

4 Claims, 6 Drawing Sheets

OTHER PUBLICATIONS

Riordan et al., Identification of the cystic fibrosis gene: cloning and characterization of complementary DNA. *Science* 245: 1066–1073, 1989.

Schoumacher et al., Phosphorylation fails to activate chloride channels from cystic fibrosis airway cells. *Nature* 330: 752, 1987.

Sigworth et al., The variance of sodium current fluctuations at the node of Ranvier. *J. Physiol.* (Lond.) 307: 97–129, 1980.

Smit, et al., Functional roles of the nucleotide–binding folds in the activation of the cystic fibrosis transmembrane conductance regulator. *Proc. Natl. Acad. Sci USA* 90: 9963–9967, 1993.

Suganuma et al., Calyculin A, an inhibitor of protein phosphotases, a potent tumor promoter on CD–1 mouse skin. *Cancer Res.* 50: 3521–3525, 1990.

Welsh et al., Molecular mechanisms of CFTR chloride channel dysfunction in cystic fibrosis. *Cell* 73: 1251–1254, 1993.

Yang et al., Modulation of CFTR chloride channels by calyculin and genistein. *Am. J. Physiol.* 272 (*Cell Physiol.* 41): C142–C155, 1997.

Hutchins, et al., Vegetables, fruits and legumes: effects or urinary isoflavonoid phytoestrogen and lignan excretion. *J. Am. Diet. Assoc.* 95:769–774, 1995.

Kavanagh, et al., Drug Disposition in Cystic Fibrosis. *Cystic Fibrosis*, edited by Pamela B. Davis, Marcel Dekker, Inc., New York, pp. 91–136, 1993.

Kiser, et al., Two–hybrid analysis of CFTR domain interactions (Abstract). *Ped. Pulman.* 513:213, 1998.

Li, et al., *Nature* 331:358, 1988.

Widdicombe, et al., *Trends in Biological Science* 16:474–477, 1991.

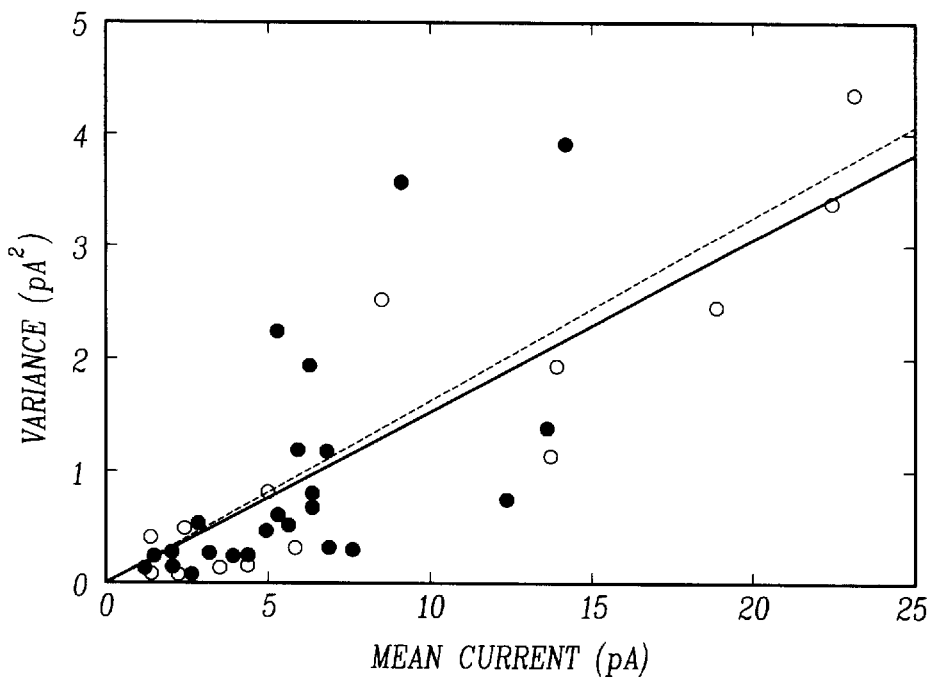
Fig-4A
Fig-4B
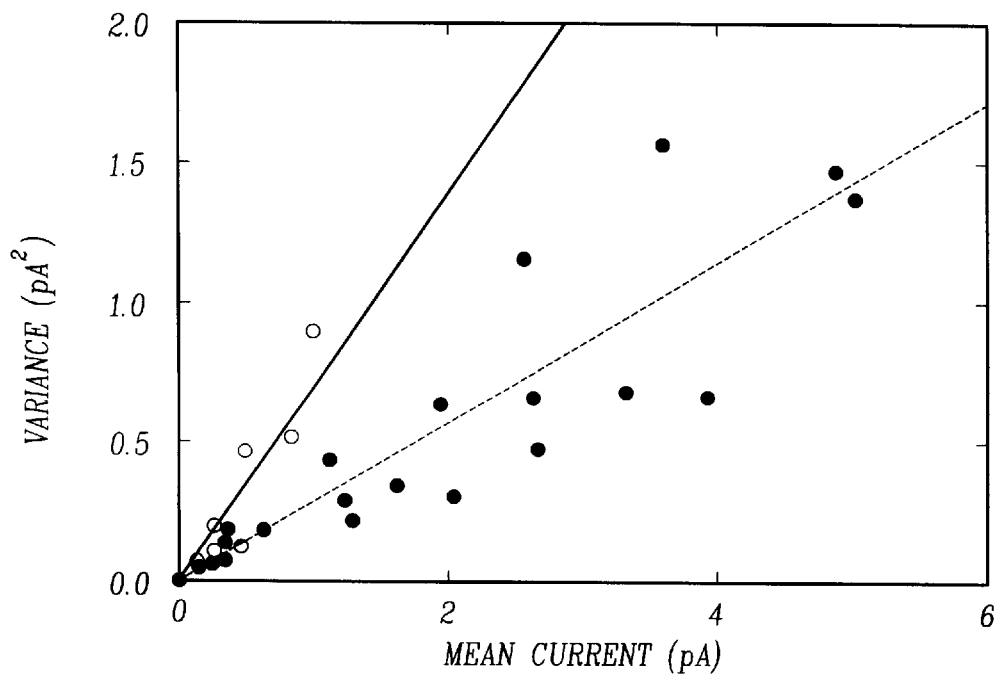

Fig-9A
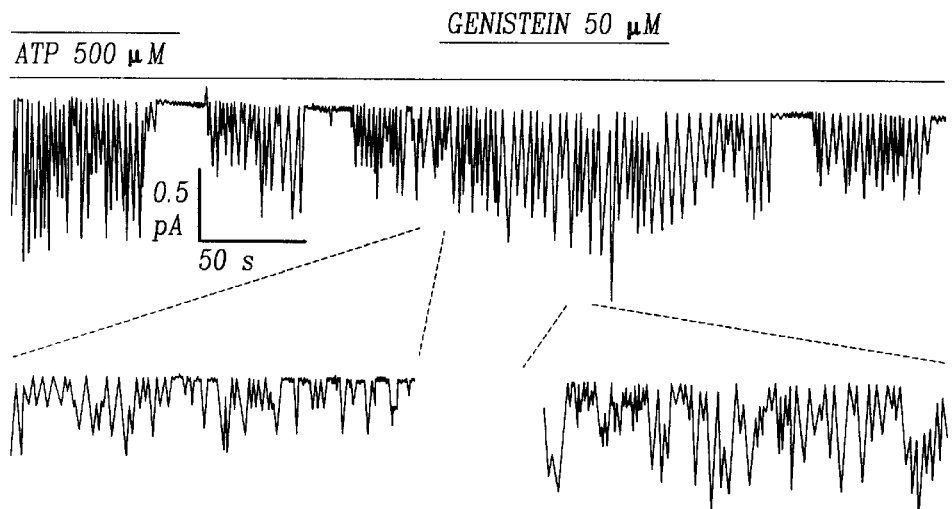
Fig-9B
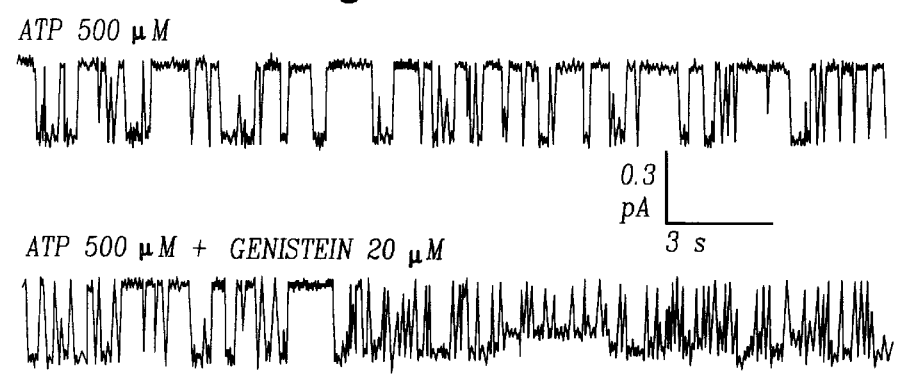
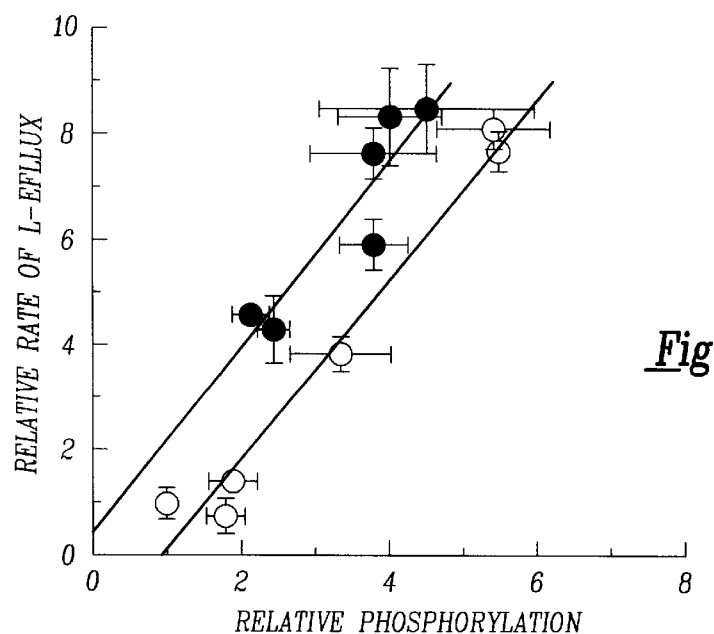
Fig-10

GENISTEIN FOR THE TREATMENT OF CYSTIC FIBROSIS

CROSS REFERENCE TO RELATED APPLICATIONS

This application claims benefit under 35 USC §119(e) of U.S. Provisional Application Serial No. 60/038,885, filed Feb. 20, 1997.

GOVERNMENT SUPPORT

Not Applicable

TECHNICAL FIELD

The present invention relates to a therapeutic treatment for cystic fibrosis, particularly to the restoration of chloride channel function caused by mutations in the protein designated Cystic Fibrosis Transmembrane Conductance Regulator (CFTR).

BACKGROUND OF THE INVENTION

Field of the Invention

Cystic fibrosis (CF) is the most common fatal genetic disease among persons of Caucasian origin. The frequency of the disease in this population is approximately 1 in 2500 live births [Boat et al., 1989], which translates into a carrier frequency of approximately 1 in 25. CF is associated with a wide-spread defect in the secretory processes of all secretory epithelia. Patients with CF, who rarely live for more than 30 years, exhibit abnormalities in a variety of respiratory, gastrointestinal and genitourinary tract systems, as well as elevated sweat electrolyte concentrations. Patients with CF exhibit abnormally viscid mucous secretions that block the airways and the pancreatic ducts. The blockage of the airways and pancreatic ducts are responsible for the two most clinically important manifestations of CF, that being chronic pulmonary infection and pancreatic insufficiency. The damage to the pancreas resulting in over 80% pancreatic insufficiency occurs in utero.

The above manifestations appear related to abnormal ion transport in the secretory epithelia of the affected organ [Quinton, 1983; Knowles et al., 1983; Frizzell et al., 1986; Boucher et al., 1986; Quinton, 1990]. This was shown in the identification of reduced chloride permeability in isolated sweat ducts and nasal epithelia of patients with CF. This observation led to the conclusion that a fundamental defect in the transport of chloride (Cl) ions, and possibly other ions, across epithelial cells must exist.

The relative impermeability of epithelial cell membranes to Cl ions appears to be the primary defect in CF. The molecular basis (the gene) for this defect in Cl ion transport was mapped and identified in 1989 [Riordan et al, 1989]. The protein product of the CF-associated gene is designated the Cystic Fibrosis Transmembrane Conductance Regulator (CFTR). The CFTR protein is a single protein of approximately 170 kd and is made up of two repeated elements, each comprising six transmembrane segments and a nucleotide binding domain. The two repeats are separated by a large, polar, domain, designated R, containing multiple potential phosphorylation sites.

Normal CFTR protein in healthy individuals is found on the apical portion of epithelial cells which line the airway, gastrointestinal tract, and other ducts in the body. The CFTR chloride channel is activated by protein kinase A (PKA)-dependent phosphorylation and gated by the hydrolysis of ATP in two nucleotide binding domains, NBD1 and NBD2 [Gadsby et al., 1995; Riordan et al, 1989].

The most common mutation in CFTR responsible for CF disease is a deletion of three nucleotides that encode a single amino acid (phenylalanine) at amino acid position 508. This mutation is designated "ΔF508," and is associated with approximately 70% of the cases of cystic fibrosis, the remaining 30% have mutations elsewhere. The ΔF508 mutation results in an abnormal folding of the CFTR protein which is thought to be responsible for the improper localization of a large portion of the mutant ΔF508 CFTR.

The mutations in the CFTR reduce the chloride channel activity [Collins, 1992; Welsh et al., 1993]. Misfolded ΔF508 is targeted for degradation in the endoplasmic reticulum; thus the predominant form of the ΔF508-CFTR is decreases in the apical membrane [Cheng et al., 1992].

The mutant CFTR protein ΔF508 CFTR has been shown to be synthesized in CF cells; however, a large part is retained in the cell where it appears to be rapidly degraded. Studies have shown that the ΔF508 CFTR protein possesses functional characteristics similar to those of the normal CFTR protein in constructed lipid bilayers, but that a large portion simply does not reach the correct cellular location of the cell surface. [Cheng et al., 1990; Denning et al. 1992, Li et al., 1993; Yang et al., 1993]. That portion of ΔF508 CFTR which does reach the apical portion of the cell is not activated by drugs which activate protein kinase.

Current therapies for the treatment of CF include physical therapy, nutritional therapy and antibiotic therapy [Ramsey, 1996]. These treatments are all directed toward treatment of the symptoms or effects of the disease and target the secondary effects of the disease; namely, obstructed airways, malnutrition, and chronic bacterial infections in the lungs. None of these approaches address the primary defect of the disease, the mutant CFTR protein and thereby the reduced chloride channel activity.

Recent discoveries have been used to attempt to treat CF including gene therapy and compounds which elevate cAMP levels. These approaches have not been successful. A new therapeutic modality or agent for the treatment of CF which is targeted to treating the underlying molecular dysfunction at the chloride channel level, would be highly desirable.

Furthermore, it would be useful to have additional therapeutic methods and compositions which can be used as drugs to restore the chloride channel function in cells with mutant CFTR, thereby providing a modality for treating Cystic Fibrosis at the level of restoring chloride channel function to mutant CFTR and which can be used in combination with other currently available therapeutics.

SUMMARY OF THE INVENTION AND ADVANTAGES

According to the present invention, a method of treating CF using genistein is disclosed. The use of genistein, and derivatives and analogues thereof, has a restorative effect on the chloride channel function in cells with mutant CFTR. Genistein can be used to stimulate mutant CFTR cells and can therefore be used to treat Cystic Fibrosis. This effect is novel and independent of genistein activity as a protein tyrosine kinase inhibitor.

The present invention also provides a therapeutic composition for treating a subject having CF. The composition consists of a therapeutically effective amount of genistein, and derivatives and analogues thereof, and a pharmaceutically acceptable carrier which when administered to a patient improves mutant CFTR function.

DESCRIPTION OF THE DRAWINGS

Other advantages of the present invention will be readily appreciated as the same becomes better understood by reference to the following detailed description when considered in connection with the accompanying drawings wherein:

FIGS. 4A and B are graphs showing the variance analysis of macroscopic currents for wt- and ΔF508-CFTR wherein (A) is a plot of variance as a function of mean-current amplitude for NIH/3T3-CFTR(●) and NIH/3T3-ΔF508 (○) cells stimulated with 10 μM forskolin plus 50 μM genistein. (B) is a plot of variance as a function of mean-current amplitude for NIH/3T3-CFTR (●) and NIH/3T3-ΔF508 (○) cells stimulated with 10 μM forskolin. Lines are least square regressions.

FIGS. 9A and B are recordings of the effects of genistein on CFTR gating in excised inside-out patches from NIH/3T3-CFTR or NIH/3T3-ΔF508 cells. CFTR channels were activated by 10 μM forskolin +20 nM calyculin A before excision into an inside-out configuration. Presence of calyculin A helps to slow channel dephosphorylation. (A): continuous 14.5 minute recording of a patch containing wt-CFTR. Expanded traces are 22 seconds in length. ATP (500 μM) with or without 20 μM genistein was present as indicated. (B): 2 traces of 44 seconds in length of an excised inside-out patch with CFTR-ΔF508.

FIG. 10 is a graph showing the effects of genistein on CFTR phosphorylation and channel activity. In parallel experiments I⁻ efflux and in vivo phosphorylation of CFTR were measured in NIH/3T3-CFTR cells. Assays are performed at forskolin concentrations between 0 and 10 μM and in the presence (filled symbols) or absence (open symbols) of 50 μM genistein. CFTR activity and phosphorylation in the absence of either agonist were assigned a value of 1.0, and, for each experimental condition, relative values of I⁻ efflux were plotted against relative levels of CFTR phosphorylation. Error bars are±SE for n>4. Lines were fit by least squares.

DETAILED DESCRIPTION OF THE INVENTION

Figure 1:
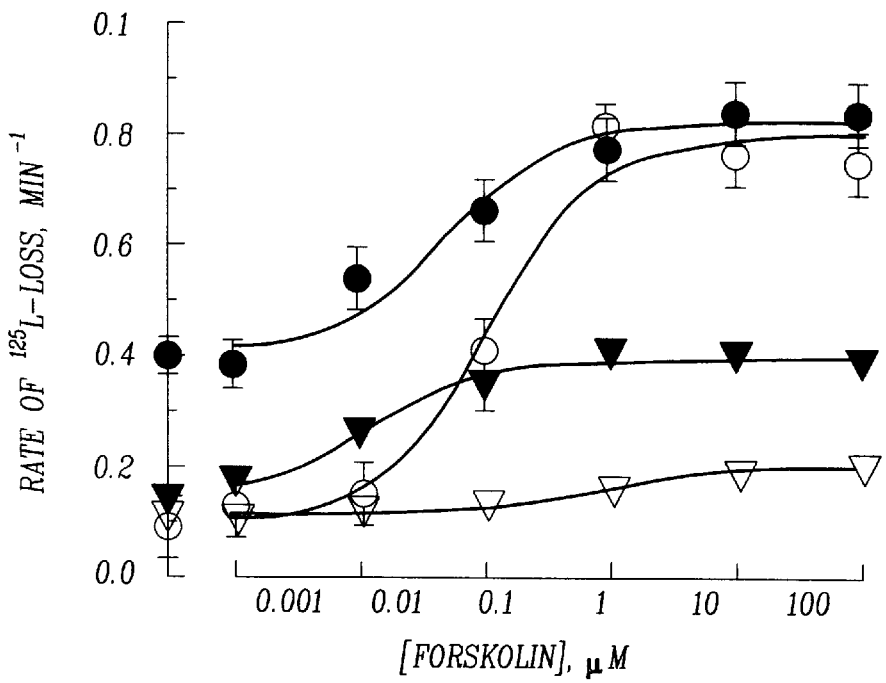
FIG. 1 is a graph representing the dose-responses relationship for forskolin-dependent I⁻ efflux. Peak rates of I⁻ efflux in the presence (closed symbols) or absence (open symbols) of 50 μM genistein were obtained with NIH/3T3-cystic fibrosis transmembrane conductance regulator (NIH/3T3-CFTR) (circles) and NTH/3T3-Δphenylalanine 508 (ΔF508) cells (triangles). NIH/3T3-CFTR cells are cultured at 37° C. NIH/3T3-Δ508 cells are cultured at 27° C. for 3 days prior to assay. Data are mean values±SE (n>5). Lines were fit by nonlinear least squares.
Figure 2:
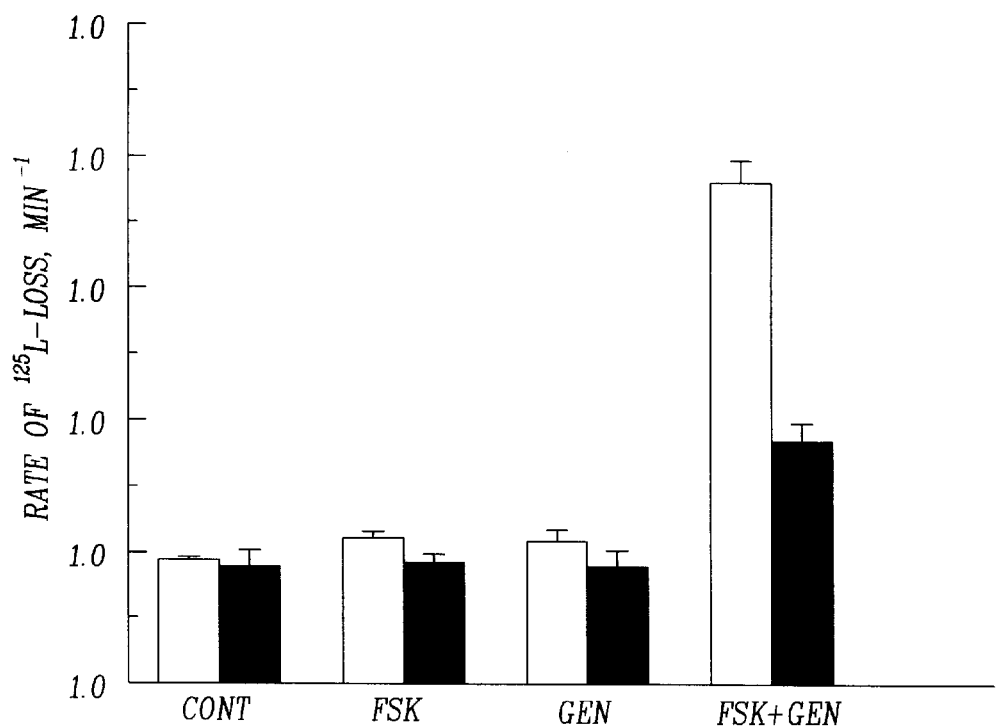
FIG. 2 is a bar graph showing the effects of stimulation of ΔF508-CFTR by forskolin and genistein. Peak rates of I⁻ efflux were measured with NIH/3T3-ΔF508cells that were cultured at 37° C. (open bars) or at 27° C. for 3 days prior to assay (filled bars). I⁻ efflux was assayed without added agonist as a control and with 1 μM forskolin (fsk), 50 μM genistein (gen), or 1 μM forskolin plus 50 μM genistein (fsk+gen). Error bars are SE for n>7.

According to the present invention, a method for treating Cystic Fibrosis is provided. The method comprises administering to a person afflicted with that condition an effective amount of genistein (4',5,7-trihydroxyisoflavone) or an analogue or derivative thereof is used.

Genistein, and derivatives and analogues thereof, can be administered in combination with other drugs or singly consistent with good medical practice. The other drugs can include, for example, antibiotics or nutritional therapies. Antibiotics are often administered to individuals with Cystic Fibrosis because of the common bacterial infections which occur in those afflicted with Cystic Fibrosis.

Genistein is an isoflavone that is abundant in legumes [Hutchins et al., 1995]. Genistein inhibits several ATP-binding enzymes (Akiyama et al., 1987; Huang, et al., 1992; Markovitz et al., 1989), including tyrosine kinases [Akiyama et al., 1987], and acts as a chemokine in both humans and rats [Collins, 1992; Berger et al, 1991]. Genistein also activates wt-CFTR chloride channels in a variety of cells [Illek et al., 1996; Reenstra et al., 1996; Yang et al., 1997, Markovitz et al, 1989; Lehrich et al., 1995]. Although the molecular mechanism for genistein-dependent activation of wt-CFTR has not been established, recent data suggest that genistein might inhibit wt-CFTR dephosphorylation [Illek et al., 1996; Reenstra et al., 1996; Yang et al., 1997]. First, biochemical measurements of wt-CFTR phosphorylation show that genistein increases the steady-state phosphorylation level of wt-CFTR [Reenstra et al., 1996] but does not increase cAMP levels or PKA activity [Illek et al., 1995; Reenstra et al.,1996]. Second, genistein, stimulates basal wt-CFTR activity [Illek et al, 1995; Yang et al., 1997] but does not appear to activate the channel in cells that lack a basal CFTR activity [Yang et al., 1997]. Third, genistein potentiates cAMP-dependent wt-CFTR channel activity [Yang et al., 1997]. Fourth, genistein prevents deactivation of wt-CFTR channel currents after removal of cAMP-dependent stimulation [Illek et al., 1996; Yang et al., 1997]. A direct inhibition of protein phosphatases by genistein has been suggested [Illek et al., 1996; Reenstra et al., 1996], but no protein phosphatase has been shown to be inhibited by genistein.

It is presently known in the art that genistein effectively inhibits acid secretion and osteopathic bone resorption [U.S. Pat. No. 5,506,211, incorporated herein by reference, see particularly column 1, lines 58–60]. The ability of a genistein analogue to inhibit tyrosine kinase has been shown in U.S. Pat. No. 5,506,211, incorporated herein by reference. Genistein is known to be used in treating several diseases and disorders as was shown in U.S. Pat. No. 5,506,211.

The result, as shown herein, that genistein does activate and have a restorative effect on the ΔF508-CFTR was unexpected. As discussed herein, genistein has been shown to have an effect on non-mutant (normal) CFTR and a better effect on "mutant" CFTR. In other studies, activation of apical chloride channels in epithelial cells [Frizell et al., 1986; Schaumaeher et al., 1987; Li et al., 1991; Widdicombe et al., 1991] effects of cAMP were seen on normal (wild-type) CFTR but when tested on mutant CFTR nothing was observed. For example, as shown herein (Example 1) ΔF508-CFTR is poorly activated by the cAMP pathway, the major cellular mechanism which affects CFTR activity. Forskolin, a compound known to increase cellular cAMP concentrations, stimulates normal CFTR activity very well, but had little affect on mutant ΔF508-CFTR. Unexpectedly the use of genistein increased the effectiveness of forskolin. In the presence of genistein, ΔF508-CFTR could behave just like wt-CFTR. This ΔF508-CFTR stimulation activity is not related to genistein's activity as an inhibitor of tyrosine kinase, since genistein (and aminogenistein 4'-amino-6-hydroxyflavone) is the only protein tyrosine kinase inhibitor that has such an effect, as shown in Example 2.

The present invention provides a therapeutic composition for treating a subject having CF, by administering a therapeutically effective amount of genistein, and derivatives and analogues thereof. The therapeutic amount is sufficient to increase stimulation of an in situ mutant CFTR at the cellular location within a subject afflicted with CF. The composition consists of genistein, and derivatives and analogues thereof, and a pharmaceutically acceptable carrier which, when administered improves CFTR function.

The genistein is administered and dosed in accordance with good medical practice [Kavanagh et al., 1993], taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved pulmonary function and to improved survival rate or more rapid recovery, or improvement or elimination of symptoms and other indicators as are selected as appropriate measures by those skilled in the art of treating cystic fibrosis. For example, the dose of genistein, independent of the route of administration will have to be adjusted because of CF-specific changes in drug metabolism and elimination [Kavanagh et al., 1993].

The term analogue as used herein is defined as a compound with a structure similar to the present (genistein), but with some differences in a component as compared to the original, and will still provide the same or better functionality, for example aminogenistein. Functionally relevant refers to the biological property of the molecule. Biologically active analogues share the effector function of the native molecule on mutant ΔF508-CFTR. The term derivative as used herein is defined as a chemical compound that may be produced from another compound of similar structure in one or more steps. Examples of this are the addition of a hydrogen group by an alkyl, aryl, ureido, acyl, or amino group to the nucleus of the molecule. Biologically active derivatives also share the effector function of the native molecule. The analogue or derivative may not retain the enzymatic activity, but will retain the therapeutic effect. The analogues and derivatives are, generally, pharmaceutically acceptable salts and esters.

In the method of the present invention, the genistein can be administered in various ways so that genistein, and the derivatives and analogues thereof, retain and deliver the pharmaceutical and therapeutic activity. The preferred method of administration, particularly to address pulmonary function, is by topical application of the compound to the epithelium including aerosolization and delivered intranasally or into the paranasal sinuses. It should be noted that the genistein can be administered as the compound or as pharmaceutically acceptable salt and can be administered alone or as an active ingredient in combination with pharmaceutically acceptable carriers, diluents, adjuvants and vehicles.

The genistein compounds can be administered orally, subcutaneously or parenterally including intravenous, intraarterial, intramuscular, and intraperitoneally. Implants of the compounds may also be useful. The patient being treated is a warm-blooded animal and, in particular, mammals including man. The pharmaceutically acceptable carriers, diluents, adjuvants, and vehicles as well as implant carrier generally refer to inert, non-toxic solid or liquid filler, diluents or encapsulating material not reacting with the active ingredients of the invention.

It is noted that humans are generally treated longer than the cells exemplified herein which treatment has a length proportional to the length of the disease process and drug effectiveness. The doses may be single but are generally multiple doses over time when dealing with a chronic condition. In general, it is noted that the dosage of drugs for CF patients is based on body surface area [Kavanagh et al., 1993] and once the range is determined, as for example in a clinical trial, the dosage for each patient is calculated based on the body surface area. The frequency of daily dosing will be devised from the systemic clearance, volume of distribution and elimination half-life of genistein, a derivative or analogue thereof, with a target study-state concentration range of 25 μM. Genistein, an analogue or derivative, will be administered for the life of the patient.

When administering the genistein it will generally be formulated in a unit dosage form (solution, aerosol, suspension, emulsion). The pharmaceutical formulations suitable include sterile aqueous solutions, dispersions or aerosols and sterile powders for reconstitution into sterile solutions, aerosols or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

When delivering the genistein through aerosolization, the dosage for the aerosolite will be determined as is known in the art and exemplified in the protocols disclosed in U.S. Pat. No. 5,508,269, incorporated herein by reference.

Proper fluidity can be maintained, for example, by the use of a coating such as lecithin, by the maintenance of the required particle size in the case of dispersion and by the use of surfactants. Nonaqueous vehicles such as cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of the microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the genistein can be administered to the patient in an injectable or topical formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological composition or formulation utilized in the present invention can be administered orally to the patient. Conventional methods such as administering the compounds in tablets, suspensions, solutions, emulsions, capsules, powders, syrups and the like are usable. Known techniques which deliver orally or intravenously and retain the therapeutic activity are preferred.

As shown herein below in the examples, genistein-dependent potentiation of wt- and ΔF508-CFTR activity was measured in transfected NIH/3T3 cells. As measured by patch clamping and $I^-$ efflux, under maximal cAMP stimulation, genistein-dependent potentiation was greater for ΔF508-CFTR than for wt-CFTR. Because these studies required the use of two cell lines, NIH/3T3-CFTR and NIH/3T3-ΔF508, cultured at different temperatures, several experiments were performed to demonstrate that the observed differences in genistein-dependent potentiation were due to differences in the activity of the channel and not secondary effects of the cell line or culture conditions. Potentiation for both wt- and ΔF508-CFTR was not altered significantly by changing the culture temperature. In addition, patch-cramming experiments (FIG. 5) demonstrated that the observed differences were due to differences between these two forms of the channel and not the cell lines. Genistein-dependent potentiation of both wt- and ΔF508-CFTR was greater when assayed in cell-attached patches than when assayed by $I^-$ efflux. There does not appear to be a simple explanation for this observation but there are several differences in the experimental conditions for these two assays; these include the assay temperature, permeating ions, and the electrochemical driving force. However, in both assays, genistein-dependent potentiation of ΔF508-CFTR was greater than the potentiation of wt-CFTR.

Although several kinetic models for CFTR have been proposed [Carson et al., 1995; Gunderson et al., 1995; Hwang et al., 1994], a simplified model that is sufficient for the discussion of these results is shown in scheme 1.

Phosphorylation activation — Gating $$D \underset{k_{-1}}{\overset{k_1}{\rightleftharpoons}} P \underset{k_{-2}}{\overset{k_2}{\rightleftharpoons}} PO1 \underset{k_{-3}}{\overset{k_3}{\rightleftharpoons}} PO2$$

In this model, D and P represent dephosphorylated and phosphorylated closed states, PO1 and PO2 are two phosphorylated open states that are distinguished by differences in their mean open times, and $k_n$ are the respective rate constants. It is well established that CFTR activity requires two ATP-dependent processes, activation by kinase-dependent phosphorylation and gating by ATP hydrolysis at one or both NBDs. These two ATP-dependent steps require the presence of at least two closed states. Because nonhydrolyzable ATP analogues cannot open phosphorylated CFTR, ATP hydrolysis at NBD1 is thought to be required to open phosphorylated channels (P→PO1) [Baukrowitz et al., 1994; Hwang et al., 1994]. ATP binding/hydrolysis and channel opening are combined in $k_2$. In a similar manner, the release of ADP, $P_i$, and channel closing (PO1→P) is combined in $k_{-2}$. ATP is thought to prolong the channel opening by binding at NBD2 ($k_3$), and ATP hydrolysis ($k_{-3}$) returns the channel to the PO1 state [Hwang et al., 1994]. The hypothesis that ATP hydrolysis in NBD2 is required to close the channel is supported by the fact that in the presence of ATP nonhydrolyzable ATP analogues stabilize the open channel conformation [Hwang et al., 1994]. Results from other studies [Haws et al., 1996] and the examples herein demonstrate that CFTR channels display bursting behavior. For the model in scheme 1, this requires that $k_2$ is greater than $k_1$.

These single-channel kinetic analysis set forth in the Example reveals the presence of two mean open times and two mean closed times and can be fit to the following model (scheme 2)

$$C1 \underset{k_{-1}}{\overset{k_1}{\rightleftharpoons}} C2 \underset{k_{-2}}{\overset{k_2}{\rightleftharpoons}} O1 \underset{k_{-3}}{\overset{k_3}{\rightleftharpoons}} O2$$

where C1 and C2 represent the two closed states, O1 and O2 represent the two open states, and $k_n$ are the respective rate constants. For this model, the two mean closed times, reflecting the life times of C1 and C2, are given by $1/(k_{-1}+k_2)$ and $(k_{-1}+k_2)/k_1k_2$, respectively. Because the CFTR shows bursting behavior with long closed times separating multiple rapid openings and closings, the longer mean closed time, $T_{C2}$, reflects the lifetime of C1, and the shorter mean closed time, $T_{C1}$, reflects the lifetime of C2. To accommodate the model in scheme 1, the C1⇌C2 transition in scheme 2 corresponds to CFTR phosphorylation and dephosphorylation (D⇌P in scheme 1). Two results support this assignment. First, for wt-CFTR, the time constant is dependent on the concentration of forskolin ($T_{C2}$=~3 seconds at 10 μM forskolin and $T_{C2}$=~22 seconds at 50 nM forskolin). Second, when PKA-phosphorylated CFTR channels were studied in excised inside-out patches, the mean closed time was hundreds of milliseconds [Gunderson et al., 1994; Li et al., 1993]. In other words, the 3-seconds $T_{C2}$ for wt-CFTR under maximal cAMP stimulation was not seen when the gating of phosphorylated CFTR by ATP is examined. Once the C1⇌C2 transition is assigned, the O1 and O2 states can be assigned to PO1 and PO2 on the basis of previous studies [Carson et al., 1995; Gunderson et al., 1995; Hwang et al., 1994].

Although valid for discussion of the results in this study, the model is clearly an oversimplification. If ATP hydrolysis is required to open or close the channel [Gadsby et al., 1995], the interconversion of states is at a steady state, not at equilibrium. The conversion of P to D is likely to involve a phosphatase and is therefore not the reverse of PKA-dependent phosphorylation $k_1$. The fact that phosphorylation occurs at multiple sites on CFTR suggests that there may be additional unresolved closed states between D and P, but the 3-seconds time constant imposes technical difficulties that preclude collecting enough events to resolve these steps. Thus $k_1$ and the long closed time constant are likely to be a function of several phosphorylation and dephosphorylation reactions. It should be noted that flickering closings [Haws et al., 1994] that might represent short-lived blocking events are not included in the analysis. However, none of these considerations affect the conclusions described below.

As show in FIG. 1, the dose-response curves for forskolin-dependent activation of wt- and ΔF508-CFTR differed. If the relationship between the concentration of forskolin and PKA activity was the same in NIH/3T3-CFTR and NIH/3T3-ΔF508 cells and the levels of ATP were similar, these differences were likely due to differences in the rate constant for channel phosphorylation or dephosphorylation ($k_1$ or $k_{-1}$). This is supported by the results in Table 1, where the major kinetic difference between wt- and ΔF508-CFTR is the long closed time constant, $T_{C2}$, which reflects mainly the phosphorylation-dependent activation step. Drumm et al. [Drum et al., 1991], using 3-isobutyl-1-methylxanthine to increase cAMP levels, have observed similar differences in dose response relationships for wt- and ΔF508-CFTR. They have pointed out that as channel phosphorylation and gating are coupled, these differences could be due to changes in either step [Smit et al., 1993]. However, since phenylalanine 508 is in NBD1, they favored effects on gating [but cf. Haws et al., 1996]. These studies by comparing both single-channel kinetics and dose-response curves demonstrate that phosphorylation-dependent activation is altered by the ΔF508 mutation. This result was unexpected, for although it is generally accepted that phosphorylation of the regulatory (R) domain affects the activity of the NBDs [Gadsby et al., 1995], evidence for the reverse interaction has not been reported. Physical and perhaps functional coupling between the R domain and both NBDs were recently suggested [Kiser et al., 1996], but these data provide evidence suggesting that structural changes in NBD1 affect the reactivity of the R domain. Thus there may be bidirectional interactions between the R domain and NBDs.

These studies also provide an explanation for seemingly contradictory data from several laboratories. It has been reported and confirmed in this study that, in cell-attached patches, the $P_o$ for wt-CFTR is greater than that for ΔF508-CFTR [Dalemans, 1991; Haws et al., 1996]. This is due in large part to a prolonged closed time for ΔF508-CFTR, first reported by Dalemans et al. [Dalemans et al, 1991] in monkey fibroblasts and later confirmed by Haws et al. [Haws et al., 1996] in transfected C127I cells. The estimation, in the example herein, of the long closed time for ΔF508-CFTR in transfected NIH/3T34 cells is about sixfold longer than the value reported by Dalemans et al. [Dalemans et al., 1991] but very close to the value of ~22 seconds reported by Haws et al. [Haws et al., 1996]. These differences are likely to reflect differences in kinase or phosphatase activity in the three cell lines [Hunter, 1995]. In contrast to these results, when Li et al. [Li et al., 1993] measured the PKA and ATP-dependent $P_o$ values for purified wt- and ΔF508-CFTR in black lipid membranes, they observed that the $P_o$ values for purified wt- and ΔF508-CFTR, 0.34±0.11 and 0.27±0.14 respectively, were not significantly difference [cf. Denning et al., 1992].

In black lipid membranes, the absence of phosphatase activity should allow PKA-dependent phosphorylation to be driven to completion so that $P_o$ is solely determined by the rate constants for gating ($k_2$, $k_{-2}$, $k_3$, and $k_{-3}$ in scheme 2). If the major kinetic difference between wt-and ΔF508-CFTR is in the phosphorylation activation step, the $P_o$ values of wt- and ΔF508-CFTR should have similar values in black lipid membranes. The result that $T_{O1}$ and $T_{O2}$ are the same for wt- and ΔF508-CFTR suggests that the values of $k_{-2}$, $k_3$, and $k_{-3}$ do not differ for wt-and ΔF508-CFTR.

Although applicants have not been able to determine the effects on $k_2$, if the data is combined with those of Li et al. [Li et al., 1993], it can be concluded that the ΔF508 mutation has minimal effects on $k_2$. Applicants have also observed similar values for the $P_o$ of wt- and ΔF508-CFTR when excised patches are examined in the presence of the phosphatase inhibitor calyculin A. Because the presence of phosphatase activity could limit channel phosphorylation in cell-attached patches and thereby reduce $P_o$, these considerations also provide an explanation for differences in the $P_o$ values of wt-CFTR in cell-attached patches and black lipid membranes or excised patches.

Figure 7:
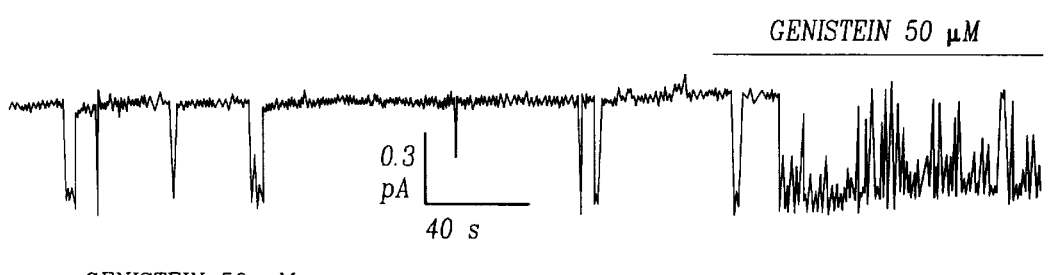
FIG. 7 is a graph showing the effects of genistein on single wt-CFTR channel activated with 50 nM forskolin. A continuous recording, 12 minutes in length, of cell-attached patch is shown. wt-CFTR was activated with 50 μM forskolin prior to start of trace and was present throughout recording Genistein (50 μM) was present as indicated. Because of the extremely long closed times, the number of events collected were not sufficient for resolving multiple kinetic components. Instead, dwell-time distributions were fit with a single exponential function obtaining a mean closed time of ~22 seconds and a mean open time of ~0.9 seconds in the presence 50 nM forskolin and a mean closed time of ~2.5 seconds and a mean open time of ~3.0 seconds in the presence of 50 nM forskolin and 60 μM genistein (cf. Table 1). Open probabilities ($P_o$) values for wt-CFTR were 0.07 in the presence of 50 nM forskolin and 0.79 in the presence of 50 nM forskolin plus 50 μM genistein.

The single-channel analysis set forth in the Example hereinbelow also suggested a mechanism for genistein-dependent activation of the CFTR. As described above, $T_{C2}=(k_{-1}+k_2)/k_1k_2$. The data demonstrate that for wt-CFTR the long closed time is increased by ~10-fold when the concentration of forskolin is reduced from 10 μM to 50 nM and that genistein dramatically decreases the long closed time (FIG. 7). Even at saturating levels of forskolin, a very long closed time was observed with ΔF508-CFTR, and genistein likely also shortens this closed time. Because genistein does not alter cellular cAMP levels or PKA activity [Reenstra et al., 1996], it is unlikely that genistein can increase the phosphorylation rate of the CFTR. However, $k_1$ is likely to be a composite rate constant for a multi-step process that involves several phosphorylation and dephosphorylation steps. Then inhibition of a dephosphorylation step can increase $k_1$ provided dephosphorylation of an intermediate is faster than phosphorylation of the intermediate. Applicants propose that genistein, by inhibiting CFTR dephosphorylation, causes an increase in $k_1$ and a decrease in $k_{-1}$. Thus the results, in the Example, are consistent with the previous conclusion that genistein inhibits CFTR dephosphorylation [Illek et al., 1996; Reenstra et al., 1996; Yang et al., 1997]. The fact that genistein decreases the long closed time for ΔF508-CFTR suggests that either the rate of a dephosphorylation step is increased relative to that of wt-CFTR or the rate of a phosphorylation step is decreased.

Although genistein-dependent stimulation of ΔF508-CFTR and wt-CFTR at low levels of PKA activity is most likely due to alterations in the rate constants for channel dephosphorylation, changes in channel phosphorylation cannot explain all of the observed effects. These include the increase in the long open time, $T_{O2}$, for wt-CFTR (Table 1), the stimulation of both wt- and ΔF508-CFTR in excised patches containing phosphorylated channels (FIG. 9) and the increased levels of wt-CFTR activity at any given level of channel phosphorylation (FIG. 10). These results are inconsistent with a mechanism that genistein solely alters CFTR dephosphorylation. Although these studies provide no direct evidence for the binding of genistein to the CFTR, it should be noted that genistein inhibits three other enzymes, tyrosine kinases [Akiyama et al., 1987], topoisomerases Markowitz et al., 1989], and histidine kinase [Huang et al., 1992], all of which hydrolyze ATP. Thus genistein may be able to interact with ATP binding sites in the CFTR.

These results provide strong evidence that genistein influences the phosphorylation activation step by inhibiting channel dephosphorylation and the ATP gating step, presumably by decreasing the rate of ATP hydrolysis. Do these two modes of effects result from two separate actions of genistein? Previous studies suggest inhibition of protein phosphatases by genistein [Illek et al., 1996; Reenstra et al., 1996; Yang et al., 1997], but no known phosphatases have been shown to be inhibited by genistein. An alternative mechanism for an apparent inhibition of phosphatase-dependent dephosphorylation could be through conformational changes induced by genistein binding to the CFTR. Thus, while inhibition of protein phosphatases by genistein cannot be ruled out, these results raise the possibility that binding of genistein to the CFTR (presumably at NBDs) facilitates PKA-dependent phosphorylation of the R domain and affects ATP hydrolysis at the NBDs. This agrees with the above conclusion that physical states of the NBD can affect phosphorylation/dephosphorylation of the R domain in the CFTR.

The above discussion provides a factual basis for the use of genistein and its derivatives or analogues, to enhance ΔF508-CFTR activity in patients with CF. The methods used with and the utility of the present invention can be shown by the following non-limiting examples and accompanying figures.

EXAMPLES

GENERAL METHODS

Cell culture: NIH/3T3-CFTR, NIH/3T3-ΔF508, and NIH/3T3 mock cells (generous gifts from Dr. Richard Mulligan of Children's Hospital and Medical Center, Harvard Medical School) were grown as described [Bradbury et al., 1992] at 37° C. and 5% $CO_2$ in Dulbecco's modified Eagle's medium-H21 supplemented with 10% new-born calf serum, 4 mM glutamine, 25 mM glucose, 100 μg/ml penicillin, 100 μg/ml streptomycin, and 50 μg/ml gentamicin. Cells were maintained in T75 flasks, passaged at 90–95% confluency, and split one to four. For measurements of $I^-$ efflux and in vivo phosphorylation, cells were seeded onto 35-mm dishes at $10^8$ cells/cm$^2$. For patch-clamp experiments, cells were grown on coverglass chips in 35-mm culture dishes. Media were replaced 24 hours after plating and thereafter every 48 hours. In all cases, media were changed on the day before $I^-$ efflux studies, NIH/3T3-ΔF508 cells were transferred to 27° C. three days before use, and 1 day prior to study, media were supplemented with 5 mM butyrate. For patch-clamp studies, where a constant level of functional ΔF508-CFTR was not essential, NIH/3T3-ΔF508 cells were cultured at 27° C. for 2–6 days before use. Calu-3 cells were grown and maintained as described by Hunter [1995].

Transient expression of wt-CFTR in HEK293 cells: The pRBG4 vector containing wt-CFTR cDNA is a generous gift from Drs. Kevin Gunderson and Ron Kopito of Stanford University. HEK293 cells were transfected with the calcium phosphate method as described previously [Gunderson et al., 1994].

$I^-$ efflux: $I^-$ efflux was measured as described previously [Reenstra et al., 1996]. Briefly, cells were incubated for 30 minutes with 37° C. $I^-$ efflux buffer [(in mM) 141 NaCl, 4 KCl, 1 $KH_2PO_4$, 0.9 $MgCl_2$, 1.7 $CaCl_2$. 10 N-2hydroxyethylpiperazine-N'-2-ethanesulfonic acid (HEPES), 25 glucose pH 7.4] containing 5 μCi/ml carrier-free $^{125}I^-$ (sodium salt). Extracellular $^{125}I^-$ was removed by washing four times with efflux buffer, and the rate of loss of intracellular $^{125}I^-$ was determined by replacing the bathing solution with 37° C. efflux buffer every 60 seconds for 12 minutes. Time-dependent rates of $^{125}I^-$ efflux are calculated from $R=\ln(^{125}I^{-t1}/^{125}I^{-}_{t2})/(t1-t2)$, where $^{125}I^{-t}$ is the intracellular $^{125}I^-$ at time t and t1 and t2 are successive time points. Dose-response curves were obtained from peak rates of 125$I^-$ efflux by nonlinear least squares fitting to $R=[R_o+R_{mx}\cdot([fsk]/K_{1/2})]/[1+([fsk]/K_{1/2})]$, where $R_o$ and $R_{mx}$ are the rates of $^{125}I$ efflux at zero and infinite concentration of forskolin (fsk), and $K_{1/2}$ is the concentration of agonist that gives a half-maximal change.

In vivo $^{32}P$-labeling: As described previously [Reenstra et al., 1996], NIH/3T3-CFTR cells were washed with efflux buffer and incubated for 90 minutes in 0.5 ml of phosphate-free efflux buffer containing 0.4 mCi/ml $^{32}P$-labeled phosphate (3,000 Ci/mmol). Incubation buffer was removed, and cells were rinsed with phosphate-free efflux buffer. Agonist was added. After 2 minutes, agonist was removed, and cells were lysed with 0.35 ml of CFTR-RIPA buffer [50 mM tris(hydroxymethyl)aminomethane (Tris), 150 M NaCl, 1 mM EDTA, 1 mM ethylene glycol-bis (β-aminoethyl ether)-N, N, N', N',-tetraacetic acid (EGTA), 0.1% sodium dodecyl sulfate (SDS), 1% sodium deoxycholate. 1% Triton X-100, 1 mM vanadate, 0.1 mM phenylmethylsulfonyl fluoride, and 0.1 mg/ml aprotinin at pH 7.5] by rocking at 4° C. for 30 minutes. Nondissolved material was pelleted by centrifugation at 100,000 g for 20 minutes. Cleared lysate was incubated at 4° C. with 1.0 μg of anti-CFTR (Genzyme, anti-COOH-terminal) for 1 hour and precipitated with 0.5 μl protein A-agarose beads (Pierce Chemical Co.). Immunoprecipitated protein was dissolved in SDS sample buffer and separated by SDS-polyacrylamide gel electrophoresis on 5% gels. Gels were dried, and phosphorylated proteins were visualized by authoradiography and quantified by scintillation counting of excised bands.

Electrophysiology: CFTR channel currents were recorded at room temperature (~22° C.) with a patch-clamp amplifier (EPC-9, Heka Electronic), filtered at 100 Hz with a built-in three-pole Bessel filter, and stored on videotapes. Data were subsequently refiltered at 25 Hz with an eight-pole Bessel filter (Frequency Device, Havervill, Mass.) and captured onto a hard disk at a sampling rate of 50 Hz. Because the mean open time and the mean closed time were in the range of several hundred milliseconds, most of the gating events were captured even with 25 Hz filtering (a $T_{10-20}$ rise time of ~15 milliseconds). Short closings, <100 milliseconds, were likely due to channel blockade by intracellular anions. The addition of a blocked state in the kinetic scheme would not have affected these conclusions. Patch-clamp electrodes were made from Corning 7052 glass capillaries (Warner Instrument, Hammed, Conn.). The pipette resistance was usually 3–5 MΩ, and the seal resistance was >20 GΩ. The pipette solution contained (in mM) 140 N-methyl-D-glucamine chloride (NMDG-Cl), 2 $MgCl_2$, 5Ca $Cl_2$, and 10 HEPES (pH 7.4 with NMDG). The superfusion solution contained (in mM) 150 $NaCl_2$, 2 $MgCl_2$, 1 EGTA, 5 glucose, and 5 HEPES (pH 7.4 with NaOH). In excised inside-out patch experiments, the bath solution contained (in mM) 130 MNDG-Cl, 10 EGTA, 10 HEPES, 20 tetraethylammonium chloride, 8 Tris, and 2 $MgCl_2$ (pH 7.4 with NMDG). Pipette potential was held at 50 mV relative to the bath. Downward deflections represent channel opening.

Reagents: Forskolin, purchased from Calbiochem (La Jolla, Calif.), was stored as 20 mM stock in dimethyl sulfoxide (DMSO)) at 4° C. Genistein was stored as 100 mM stock in DMSO at ~20° C. Genistein, purchased from LC laboratories (Woburn, Mass.), Sigma (St. Louis, Mo.), or Calbiochem, showed similar effects. For $I^-$ efflux, forskolin and genistein stocks were prepared so that the final concentration of DMSO was no more than 0.2%.

Statistics: Mean currents and variance were estimated with Igor (Wavemetrics, Lake Oswego, Oreg.). Parameters for mean current-variance relationships and dose-response curves were obtained from least-square fitting with Sigmaplot (Jandel, San Rafael, Calif.). $P_o$ was calculated from patches containing a single channel by dividing the open channel current amplitude with the mean-current amplitude. Dwell-time analysis was described previously [Baukrowitz et al., 1994]. Calculated values are presented as means±SE. Comparisons among data were made using the Student's t-test with P<0.05 considered significant.

Example 1

To investigate effects of genistein on CFTR activity, the rates of $I^-$ efflux were measured from stably transfected NIH/3T3 cells expressing wt- and ΔF508-CFTR (NIH/33-CFTR and NIH/3T3-ΔF508 cells, respectively). As shown in FIG. 1, for NIH/3T3-CFTR cells, forskolin increased the rate of $I^-$ efflux, and the maximal stimulation at 10 μM forskolin was 8.2±0.4-fold (n=8) with a $K_{1/2}$ of 0.11±0.03 μM. Genistein (50 μM) potentiated the response at low concentrations of forskolin, decreasing the $K_{1/2}$ to 0.05±0.02 μM, but had no effect at high forskolin concentrations. When forskolin-dependent channel activity was measured in NIH/3T3-ΔF508 cells that were cultured at 37° C., 10 μM forskolin increased $I^-$ efflux by <15%. To increase ΔF508-CFTR channel activity, NIH/3T3-ΔF508 cells were cultured at 27° C. for 3 days [Denning et al., 1992]. When cultured in this manner, the maximal forskolin-dependent increase in $I^-$ efflux was 1.65±0.08-fold (n=12) with a $K_{1/2}$ of 0.67±0.26 μM. Genistein (50 μM) potentiated forskolin-dependent $I^-$ efflux at all forskolin concentrations tested, increasing the maximal response by 3.7±0.4-fold and decreasing the $K_{1/2}$ to 16±5 nM. The effects of genistein are due to CFTR expression, because neither 1 μM forskolin, 50 μM genistein, nor 50 μM genistein plus 1 μM forskolin stimulated $I^-$ efflux in mock-transfected NIH/3T3 cells.

To determine whether the differences in genistein-dependent potentiation were due to differences in culture temperature, rates of $I^-$ efflux for NIH/3T3-ΔF508 cells that had been cultured at 27° C. were compared with rates for cells that had been cultured at 37° C., the potentiation of forskolin-dependent ΔF508-CFTR activity by genistein was similar to that obtained with cells cultured at 27° C.

Figure 3A:
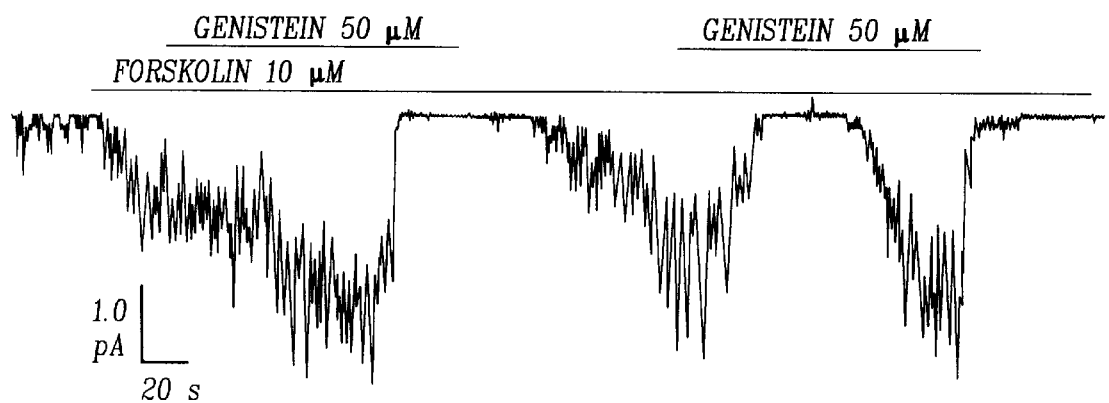
FIGS. 3A and B show recordings of the potentiation of wild-type (wt) and ΔF508-CFTR channel activity by genistein. Channels in cell-attached patches from NIH/3T3-CFTR (FIG. 3A) and NIH/3T3-ΔF508cells (FIG. 3B), were stimulated as indicated with 10 μM forskolin and 50μ genestein. With NIH/3T3-CFTR cells, channel activity was stimulated with forskolin and enhanced with genistein. Excised patch that was crammed into an adjacent cell showed similar responses to forskolin and genistein. With NIH/3T3-ΔF508 cells, sporadic opening bursts with long closings (6.1 seconds on average; Dalemans et al, 1991; Gunderson et al, 1994] were observed in the presence of forskolin alone. Actual closed time for these ΔF508 channels must be several-fold longer than this value since at least 5 channels were present in this patch.

To investigate the effects of genistein at the single-channel level, CFTR channel activity was recorded in cell-attached membrane patches. FIG. 3A shows a representative current trace from an NIH/3T3-CFTR cell. Basal CFTR activity was observed in the absence of agonists, presumably due to basal PKA activity [Messina et al., 1994; Yang et al., 1997]. Saturating forskolin (10 μM) increased wt-CFTR channel activity and 50 μM genistein in the continued presence of forskolin, potentiated forskolin-activated wt-CFTR activity. Because the number of channels in any cell-attached patch was often unknown, mean-current amplitudes were used to quantify genistein-dependent potentiation. For NIH/3T3-CFTR cells, the average increase in mean-current amplitude was 3.9±0.4-fold (n=10). Similar potentiations were seen in Calu-3 cells (3.1±0.3, n=15), a human airway epithelial cell line expressing wt-CFTR [Haws et al., 1994] and transiently transfected HEK293 cells (3.1±0.7, n=10) [Gunderson et al, 1995], suggesting that the genistein-dependent mechanism of CFTR modulation might be similar in these three systems. FIG. 3A also shows that channel activity was rapidly lost on excision of the patch into an ATP-free bath, a hallmark of the CFTR [Gadsby et al., 1995]. However, cramming the patch [Reenstra et al., 1996] into a different NIH/3T3-CFTR cell restored forskolin-dependent channel activity. The magnitude of potentiation by genistein was similar in this "transplanted" cell, demonstrating that patch cramming per se did not alter genistein-dependent potentiation of CFTR activity.

Figure 3B:
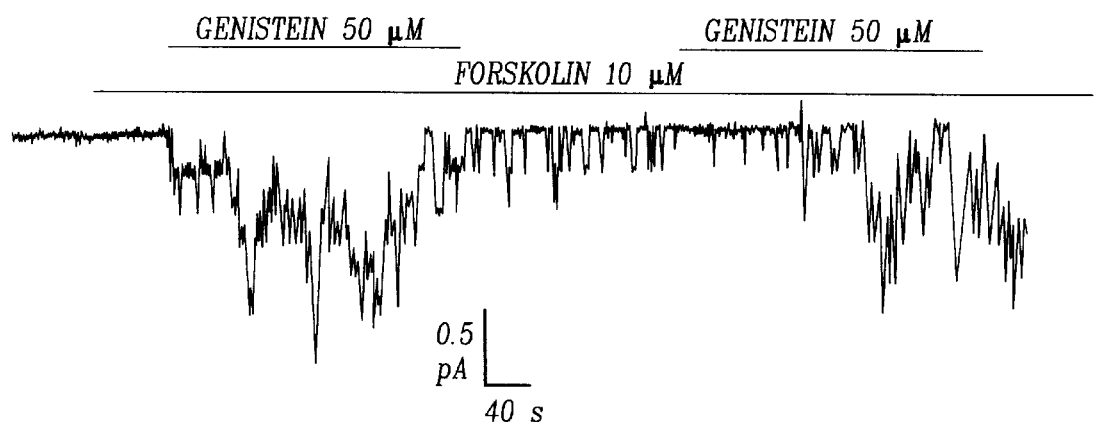

Genistein-dependent potentiation of ΔF508-CFTR activity was also examined in cell-attached patches. wt-CFTR channels were observed in >90% of patches from NIH/3T3-CFTR cells. Approximately 10% of the patches from NIH/3T3-ΔF508 cells, when grown at 37° C., showed channel activity in response to 10 μM forskolin plus 50 μM genistein. However, 54% (44 of 82) of NIH/3T3-ΔF508 patches responded to forskolin plus genistein when cells were grown at 27° C. Therefore, before patch-clamp experiments, NIH/3T3-ΔF508 cells were cultured at 27° C. for 2–6 days to increase the channel density in the plasma membrane. As shown in FIG. 3B, ΔF508-CFTR channel activity was stimulated by the addition of 10 μM forskolin and 50 μM genistein. The removal of genistein, in the continued presence of forskolin, caused a dramatic decrease in channel activity; characteristic long closed states were seen. The readdition of genistein increased the forskolin-activated ΔF508-CFTR channel current. In 23 patches, the average increase in mean-current amplitude was 18.6±2.2-fold. The increase by genistein of forskolin-dependent ΔF508-CFTR activity was significantly greater than the 3.3±0.4-fold increase for forskolin-dependent wt-CFTR activity (P<0.001).

To determine whether the increased potentiation was due to culturing cells at reduced temperature, NIH/3T3-CFTR cells were incubated at 27° C. for 2–6 days. In these cells, 50 μM genistein increased forskolin-dependent wt-CFTR activity by 3.1±0.3-fold (n=13), suggesting that the reduced culture temperature of NIH/3T3-ΔF508 cells was not responsible for the increased potentiation by genistein. Because genistein-dependent potentiation of wt-CFTR was greater at lower concentrations of forskolin (FIG. 1), 8-(4-chlorophenylthio)-cAMP (CPT-cAMP), a membrane-permeant cAMP analogue was used, to determine whether cAMP-dependent activation of ΔF508-CFTR was maximal at 10 μM forskolin. The addition of 200 μM CPT-cAMP to NIH/3T3-ΔF508 cells that had been stimulated with 10 μM forskolin failed to increase the mean-current amplitude but did not effect potentiation with genistein.

To compare genistein-dependent potentiation of wt- and ΔF508-CFTR channel activity and the $P_o$ of wt- and ΔF508-CFTR, applicants examined the mean current-variance relationships for macroscopic currents. As shown in FIG. 4A, in the presence of 10 μM forskolin and 50 μM genistein, plots of variance as a function of mean current have slopes for wt- and ΔF508-CFTR of 0.17±0.02 and 0.16±0.03 pA, respectively. Similar plots for wt- and ΔF508-CFTR in the presence of 10 μM forskolin (FIG. 4B) had slopes of 0.27±0.02 and 0.72±0.06 pA, respectively. As the slope is proportional to $(1-P_o)$ [Sigworth, 1980, these results demonstrate 1) in the presence of 10 μM forskolin, the $P_o$ of ΔF508-CFTR is lower than that of wt-CFTR; 2) genistein increases the $P_o$ of forskolin-stimulated wt- and ΔF508-CFTR; and 3) in the presence of saturating levels of forskolin and genistein, the $P_o$ of ΔF508-CFTR is not significantly different from that of wt-CFTR. These results are inconsistent with the primary effect of genistein on CFTR channel current being an increase in channel number.

Figure 5A:
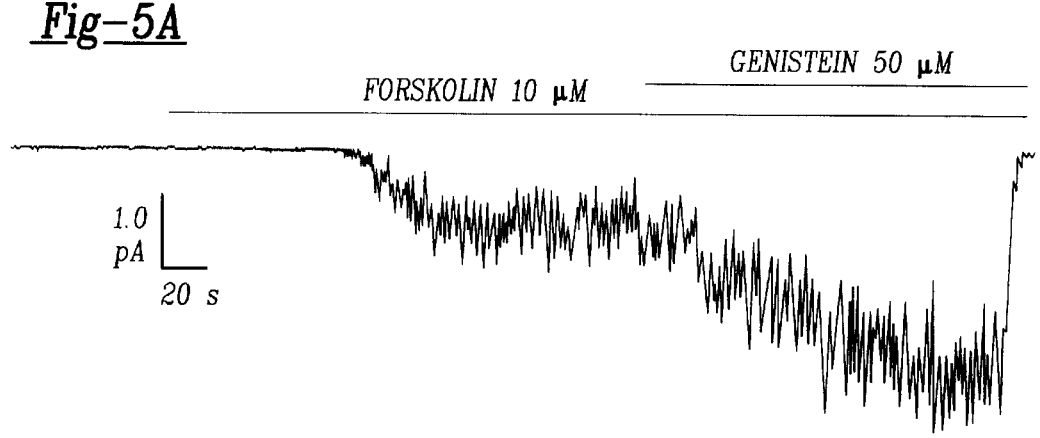
FIG. 5A and B show recordings of the potentiation of forskolin-activated wt-and ΔF508-CFTR channel activity in crammed patches. Prior to the start of the recording, cell-attached patches were excised from donor call in an inside-out configuration and crammed into recipient cell by gently placing pipette tip to cell surface of recipient cell. wt-CFTR in a NIH/3T3-ΔF508 cell (A) and ΔF508-CFTR in a NIH/3T3-CFTR cell (B) were activated by addition of 10 μM forskolin and 50 μM genistein.
Figure 5B:
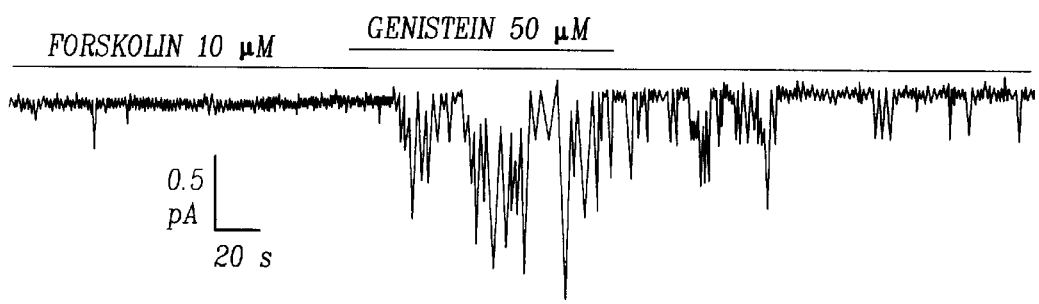

Because CF-associated mutations can alter cellular processes other than chloride transport [Barasch et al., 1991; Bradbury et al., 1992; Stutte et al., 1995] and clonal selection may affect cellular regulatory mechanisms, the observed differences in genistein-dependent potentiation of wt- and ΔF508-CFTR could be due to secondary effects and not directly related to the expression of different forms of the CFTR. To test this possibility, wt-CFTR channels were excised from NIH/3T3-CFTR cells and crammed into NIH/3T3-ΔF508 cells (FIG. 5A). The addition of forskolin induced channel activity and the subsequent addition of genistein increased the mean current by 3.2±0.3-fold (n=3). In contrast, when ΔF508-CFTR channels were excised from NIH/3T3-ΔF508 cells and crammed into NIH/3T3-CFTR cells (FIG. 5B), the addition of forskolin evoked a minimal response with characteristic prolonged channel closings. The subsequent addition of genistein enhanced ΔF508-CFTR channel activity by 19±11-fold (n=2). Thus, when either wt-CFTR channels were exposed to the cytoplasm of ΔF508-CFTR expressing cells or ΔF508-CFTR channels were exposed to the cytoplasm of wt-CFTR expressing cells, activation by forskolin and genistein was similar to activation in the native cells. These results established that the observed differences in channel activation are not due to differences in cytosolic factors and are more likely due to intrinsic differences between the two forms of the channel.

Figure 6A:
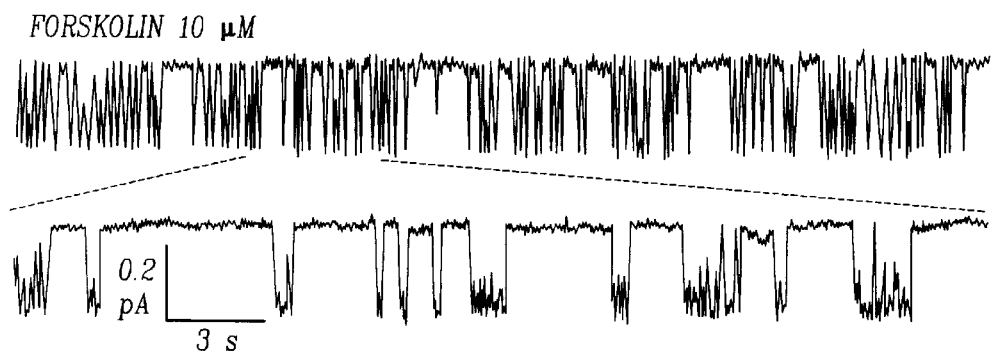
FIGS. 6A and B are recordings showing the effects of genistein on single-channel kinetics of wt-CFTR activated with 10 μM forskolin. (A): continuous recordings, 4 minutes in length, of a cell-attached patch of wt-CFTR in the presence of 10 μM forskolin or 10 μM forskolin+50 μM genistein are shown. Expanded traces, 30 seconds in length, demonstrate both short and long openings under both conditions. (B): dwell-time analysis of (A).
Figure 6A:
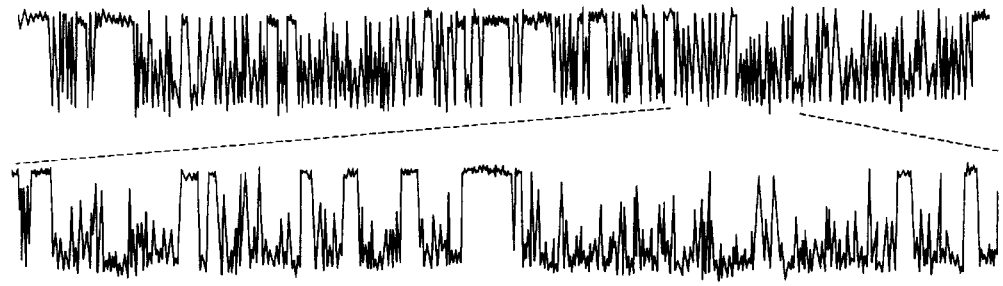
Figure 6B:
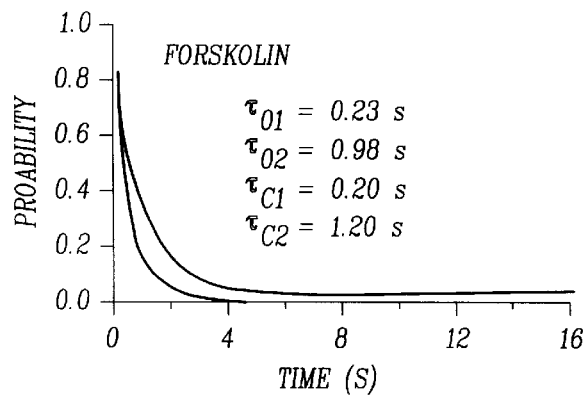
Figure 6B:
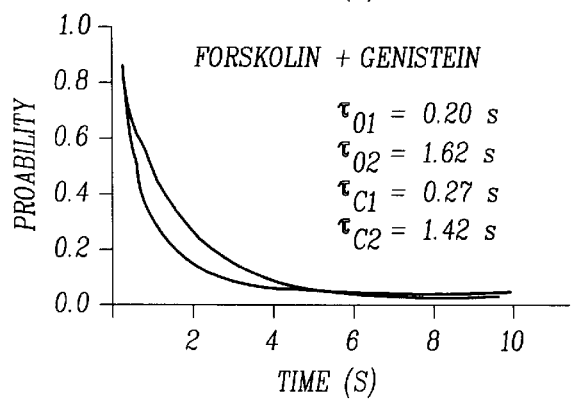

To determine how genistein increases $P_o$, the effects of genistein on single-channel kinetics were examined in cell-attached patches using dwell-time analysis. FIG. 6A shows representative traces, 4 minutes in length, of a single wt-CFTR channel. Both traces were recorded in the presence of 10 μM forskolin; 50 μM genistein was added prior to the start of the lower trace. In four wt-CFTR channels, the $P_o$ was 0.27±0.03 in the presence of 10 μM forskolin and 0.71±0.06 in the presence of 10 μM forskolin plus 50 μM genistein. Both in the presence and in the absence of genistein, the open- and closed-time distributions could be fit by double exponential functions (FIG. 6B). Best-fit values for mean open and closed times are given in Table 1. The only value that changed significantly with genistein was the long open time, $T_{O2}$, which increased by 2.4-fold. The mean open times for ΔF508-CFTR were also determined. However, since cell-attached patches containing a single ΔF508-CFTR channel were not observed, a direct assessment of the closed times for ΔF508-CFTR cannot be made. Dwell-time analysis of pooled open times were performed on 14 patches where individual openings of ΔF508-CFTR could be clearly identified. Both in the presence and in the absence of genistein, the open times for ΔF508-CFTR were not significantly different from those for wt-CFTR. Genistein increased $T_{O2}$, for ΔF508-CFTR by approximately 2.8-fold (Table 1). Based on the average observed closed time and the minimal number of channels in multi-channel patches as in FIG. 3B, $T_{O2}$ for ΔF508-CFTR in the presence of 10 μM forskolin was estimated to be about 30 seconds. Because genistein increased $T_{O2}$, of forskolin-activated ΔF508-CFTR channel current by about two-to threefold, much of the 19-fold increase in forskolin-activated ΔF508-CFTR macroscopic current with genistein must be attributed to an effect on the long closed time, $T_{O2}$.

Figure 8:
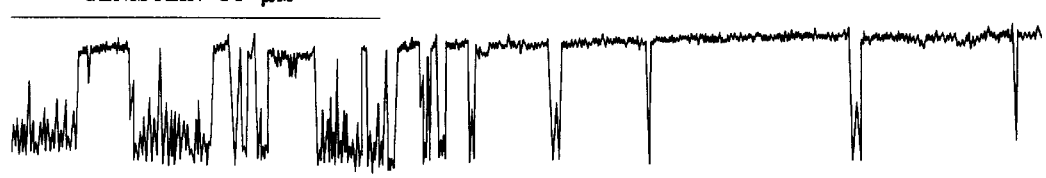
FIG. 8 is a recording of the effects of genistein on macroscopic wt-CFTR current activated with 50 nM forskolin. A continuous 12.5 minute recording of a cell-attached patch from a NIH/3T3-CFTR cell is shown. In the presence of 50 nM forskolin, $\leq 4$ single-channel current steps were observed. During 3 brief applications of 5 μM genistein, macroscopic currents of ~7.5 pA were seen.
Figure 8:
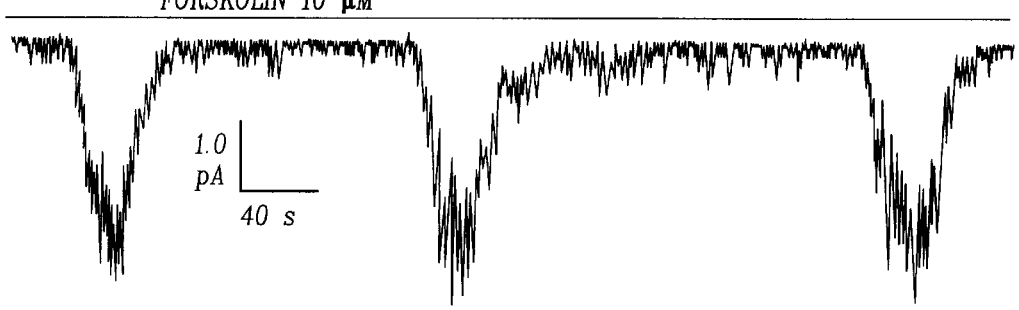

Because, as measured by I⁻ efflux (FIG. 1A), potentiation by genistein of wt-CFTR channel activity at low forskolin concentrations was larger than that in the presence of maximal stimulation with forskolin, the effects of genistein were tested on wt-CFTR activated by 50 nM forskolin (FIG. 7). At this concentration of forskolin, the $P_o$ was dramatically reduced, and prolonged closed events were seen. Although the number of opening and closing events was not large enough for dwell-time analysis, it is apparent that in this patch containing a single channel, genistein increased the open time and decreased the closed time, resulting in a >10-fold increase in the $P_0$. In experiments where multi-channel patches were activated with 50 nM forskolin, genistein increased wt-CFTR current by 21±6-fold (n=6). FIG. 8 shows the effect of 5 μM genistein on wt-CFTR channels that were activated with 50 nM forskolin. Thus, at both microscopic and macroscopic levels, wt-CFTR, when stimulated with low concentrations of forskolin, mimicked ΔF508-CFTR, in that the $P_o$ was low, prolonged closed times were seen, and genistein dramatically potentiated forskolin-dependent activation by decreasing the closed time and increasing the open time.

Because genistein induced long openings like nonhydrolyzable ATP analogues [Hwang et al., 1994], applicants tested the hypothesis that genistein effects the gating step (scheme 1) by binding to the CFTR. Channels were first activated in cell-attached patches with forskolin plus calyculin A, a membrane-permeant phosphatase inhibitor [Suganuma et al., 1991]. Patches were then excised into an inside-out configuration. CFTR channel activity depended on the presence of ATP (FIG. 9A). Genistein (50 μM) did not open wt-CFTR channels in the absence of ATP, but it increased ATP-induced currents by 2.2±0.1-fold (n=8). Because genistein did not increase single-channel amplitude and the number of functional (phosphorylated) channels was determined before the patch was excised into a PKA-free bathing solution, the twofold increase in macroscopic current must reflect a twofold increase in the $P_o$. As shown in FIG. 9B, genistein enhanced ATP-dependent ΔF508-CFTR channel current to a similar extent (2.3±0.5-fold, n=7). For both wt- and ΔF508-CFTR, the increase in $P_o$ was due to an increase in channel open time (from 302±2 milliseconds to 2,033±173 milliseconds).

As these kinetic studies suggested that genistein increased the activity of a phosphorylated form of the CFTR, a biochemical approach was also undertaken. In vivo phosphorylation of the CFTR was assayed by incubating NIH/3T3-CFTR cells with $^{32}P_i$. Cells were then stimulated with 0–10 μM forskolin or forskolin plus 50 μM genistein under the same experimental conditions used to measure I⁻ efflux shown in FIG. 1. Cells were lysed, the CFTR was immunoprecipitated and resolved by polyacrylamide gel electrophoresis, and phosphorylation was quantified. In parallel experiments, I⁻ efflux was measured. For each concentration of forskolin and genistein, relative rates of I⁻ efflux were plotted against relative levels of CFTR phosphorylation. As shown in FIG. 10, at all levels of CFTR phosphorylation, channel activity was greater in the presence of genistein. Data in the presence and absence of genistein had significantly different intercepts (P<0.05). This result is not consistent with a mechanism where the sole effect of genistein is to alter CFTR phosphorylation by modulating protein phosphatase or PKA activity. Thus the biochemical data also suggest that genistein increases the activity of a phosphorylated form of the CFTR.

Example 2

Based on the results of Example 1 other protein tyrosine kinase inhibitors were tested using the methodology of Example 1. Tyrphostin and quercetin, both tyrosine kinase inhibitors, were tested and failed to enhance CFTR activity. Other protein tyrosine kinase inhibitors which failed to activate ΔF508-CFTR include daidzein, damnacanthal, emodin, erbstatin analogue, geldanamycin, herbimycin A, lavendustin A and B, lavendustin C methyl ester, piceatannol, PP1, ST638 and HNMP-A (AM)$^3$.

Throughout this application, various publications are referenced by author and year. Full citations for the publications are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

|  | $T_{O1}$ | $T_{O2}$ | $T_{C1}$ | $T_{C2}$ |
|---|---|---|---|---|
| wt-CFTR |  |  |  |  |
| Forskolin (10 μM) | 0.24 ± 0.01 | 0.88 ± 0.09 | 0.39 ± 0.11 | 2.98 ± 0.81 |
| Forskolin (10 μM) +Genistein (50 μM) | 0.28 ± 0.11 | 2.10 ± 0.30* | 0.49 ± 0.08 | 3.76 ± 1.09 |
| ΔF508-CFTR |  |  |  |  |
| Forskolin (10 μM) | 0.30 ± 0.11 | 0.92 ± 0.12 |  | >30† |
| Forskolin (10 μM) +Genistein (50 μM) | 0.31 ± 0.17 | 2.63 ± 0.37 |  |  |

Table 1. Values are means±SE. Patches containing a single channel are very rare. We therefore combined data from 3 different systems: Calu-8 (n=2), NIH/3T3-cystic fibrosis transmembrane regulatory protein (CFTR) (n=1), and HEK293 (n=1) cells. Because of the heavy filtering, closings that are <100 ms were not considered as closed events in the dwell-time analysis. ■<0.05. †Estimation of long closed time ($T_{C2}$) was made from observed closed time and minimum number of channels in multichannel patches like the one in FIG. 3B.

REFERENCES

Akiyama et al., Genistein, a specific inhibitor of tyrosine-specific protein kinases. J. Biol. Chem. 282: 5592–5595, 1987.

Baukrowitz et al., Coupling of CFTR Cl channel gating to an ATP hydrolysis cycle Neuron 12: 473–482, 1994.

Berger et al., Identification and regulation of the cystic fibrosis transmembrane conductance regulator-generated chloride channel. J. Clin. Invest. 88: 1422–1431, 1991.

Bradbury et al., Regulation of plasma membrane recycling by CFTR, Science 258: 530–582, 1992.

Carson et al., The two nucleotide-binding domains of cystic fibrosis transmembrane conductance regulator (CFTR) have distinct functions in controlling channel activity. J. Biol. Chem. 270: 1711–1717, 1995.

Cheng et al., Defective intracellular transport and processing of CFTR is the molecular basis of most cystic fibrosis. Cell 65: 827–834, 1990.

Collins et al., Cystic Fibrosis: molecular biology and therapeutic implications, Science 256: 774–779, 1992.

Dalemans et al., Altered chloride ion channel kinetics associated with the ΔF508 cystic fibrosis mutation. Nature 354: 526–528, 1991.

Denning et al., Processing of mutant cystic fibrosis transmembrane conductance regulator is temperature-sensitive. Nature 358: 761–764, 1992.

Drumm et al., Chloride conductance expressed by ΔF508 and other mutant CFTRs in Xenopus cocytes. Science 254: 1797–1799, 1991.

Frizell et al., Science 233: 558, 1986.

Gadsby et al. The CFTR chloride channel of mammalian heart. Annu. Rev. Physiol. 57: 387–416, 1995.

Gunderson et al., Confrontational states of CFTR associated with channel gating; the role of ATP binding and hydrolysis. Cell 82: 231–239, 1995.

Gunderson et al., Effects of pyrophosphate and nucleotide analogs suggest a role for ATP hydrolysis in cystic fibrosis transmembrane regulator channel gating. J. Biol. Chem. 269: 19349–19353, 194.

Haws et al., CFTR in Calu-3 human airway cells; channel properties and role in cAMP-activated Cl conductance. Am. J. Physiol. 266 (Lung Cell, Mol. Physiol 10): L502–L512, 1994.

Haws et al., ΔF508-CFTR channels: kinetics, activation by forskolin, and potentition by xanthines. Am. J. Physiol. 270 (Cell Physiol. 39): C1544–C1555, 1996.

Huang et al., Genistein inhibits protein histidine kinase. J. Biol. Chem. 267: 15511–15515, 1992.

Hunter, Protein kinases and phosphates: the Yin and Yang of protein phosphorylation and signaling. Cell 80: 225–236, 1995.

Hutchins et al., Vegetables, fruits, and legumes: effects on urinary isoflavonoid phytoestrogen and lignan excretion. J. Am. Diet. Assoc. 95: 769–774, 1995.

Hwang et al., Regulation of gating of CFTR Cl channel by phosphorylation and ATP hydrolysis. Proc. Natl. Acad. Sci USA 91: 4698:4702, 1994.

Illek et al, Alternate stimulation of apical CFTR by genistein in epithelia. Am. J. Physiol. 270 (Cell Physiol. 39): C265–C275, 1996.

Illek et al., Cyclic AMP-independent activation of CFTR Ol channels by the tyrosine kinase inhibitor genistein. Am. J. Physiol. 258 (Cell Physiol. 37): C886–C893, 1995.

Kavanagh et al., Drug Disposition in Cystic Fibrosis. Cystic Fibrosis, edited by Pamela B. Davis, Marcel Dekker, Inc., New York, pages 91–136, 1993.

Kiser et al., Two-hybrid analysis of CFTR domain interactions (Abstract). *Ped. Pulman.* 513: 213, 1998.

Lehrich et al., Tyrosine phosphorylation is a novel pathway for regulation of chloride secretion in shark rectal gland. *Am. J. Physiol.* 269 (*Renal Fluid Electrolyte Physiol.* 38): F594–F600, 1995.

Li et al., *Nature* 331: 358, 1988.

Li et al., The cystic fibrosis mutation (ΔF508) does not influence the chloride channel activity of CFTR *Nat. Genet.* 8: 311–316, 1993.

Markovits et al., Inhibitory effects of the tyrosine kinase inhibitor genistein on mammalian DNA topoisomerase II. *Cancer Res.* 49: 5111–5117, 1989.

Messina et al., Soy intake and cancer risk: review of in vitro and in vivo data. *Nutr. Cancer* 21: 113–131, 1994.

Ramsey. Management of pulmonary disease in patients with cystic fibrosis. *NEJM.* 335: 179–188, 1996.

Reenstra et al., CFTR chloride channel activation by genistein: the role of serine/threonine protein phosphatases. *Am. J. Physiol.* 271 (*Cell Physiol.* 40): C650–C657, 1996.

Riordan et al., Identification of the cystic fibrosis gene: cloning and characterization of complementary DNA. *Science* 245: 1068–1073, 1989.

Schaumaeher et al., *Nature* 330: 752, 1987.

Sigworth et al., The variance of sodium current fluctuations at the node of Ranvier. *J. Physiol.* (Lond.) 307: 97–129, 1980.

Smit., et al., Functional roles of the nucleotide-binding folds in the activation of the cystic fibrosis transmembrane conductance regulator. *Proc. Natl. Acad. Sci USA* 90: 9963–9967, 1993.

Suganuma et al., Calyculin A, an inhibitor of protein phosphotases, a potent tumor promoter on CD-1 mouse skin. *Cancer Res.* 50: 3521–3525, 1991.

Welsh et al., Molecular mechanisms of CFTR chloride channel dysfunction in cystic fibrosis. *Cell* 73: 1251–1254, 1993.

Widdicombe et al., *Trends in Biological Science* 16: 474, 1991.

Yeng et al., Modulation of CFTR chloride channels by calyculin and genistein. *Am. J. Physiol.* 272 (*Cell Physiol.* 41): C142–C155, 1997.

What is claimed is:

1. A method for treating cystic fibrosis by inducing cystic fibrosis transmembrane conductance regulator function in a cell containing a mutant cystic fibrosis transmembrane conductance regulator, comprising:

administering to a person afflicted with cystic
fibrosis an effective amount of genistein or an analogue or derivative thereof.

2. The method of claim 1, wherein the genistein is an analogue of genistein.

3. The method of claim 2, wherein the analogue is aminogenistein.

4. The method of claim 1, wherein the genistein is an derivative of genistein.

* * * * *